(12) United States Patent
Jääskeläinen

(10) Patent No.: US 10,585,038 B2
(45) Date of Patent: Mar. 10, 2020

(54) LIGHT ARRANGEMENT FOR AN OPTICAL DEVICE FOR MEASUREMENT OF AN INDEX OF REFRACTION, AND A REFRACTOMETER

(71) Applicant: VAISALA OYJ, Helsinki (FI)

(72) Inventor: Juha Jääskeläinen, Vantaa (FI)

(73) Assignee: VAISALA OYJ, Helsinki (FI)

( * ) Notice: Subject to any disclaimer, the term of this patent is extended or adjusted under 35 U.S.C. 154(b) by 0 days.

(21) Appl. No.: 16/447,136

(22) Filed: Jun. 20, 2019

(65) Prior Publication Data

US 2019/0391074 A1   Dec. 26, 2019

(30) Foreign Application Priority Data

Jun. 21, 2018 (FI) ..................................... 20185566

(51) Int. Cl.
*G01N 21/41* (2006.01)
*F21V 8/00* (2006.01)
(Continued)

(52) U.S. Cl.
CPC ....... *G01N 21/4133* (2013.01); *G01N 21/431* (2013.01); *G02B 6/0008* (2013.01); *G02B 6/04* (2013.01); *G01N 2021/432* (2013.01)

(58) Field of Classification Search
CPC ........ G02B 5/02; G02B 5/0205; G02B 5/021; G02B 5/0215; G02B 5/0221; G02B 5/0226; G02B 5/0231; G02B 5/0236; G02B 5/0242; G02B 5/0247; G02B 5/0252; G02B 5/0257; G02B 5/0263; G02B 5/0268;
(Continued)

(56) References Cited

U.S. PATENT DOCUMENTS 2,992,587 A * 7/1961 Hicks, Jr. .................. G02B 6/06
385/116
3,598,467 A * 8/1971 Pearson .................... G02B 6/06
359/27
(Continued)

FOREIGN PATENT DOCUMENTS

JP   H06052238 B2   7/1994
JP   2997173 B2   1/2000
(Continued)

OTHER PUBLICATIONS

Search Report dated Jan. 10, 2019, by the Finnish Patent Office for Application No. 20185566.
(Continued)

*Primary Examiner* — Gordon J Stock, Jr.
(74) *Attorney, Agent, or Firm* — Buchanan Ingersoll & Rooney PC

(57) ABSTRACT

The present disclosure relates to light arrangement for an optical device for measurement of an index of refraction, having a light source, a fiber bundle arrangement for transmitting light from the light source, a diffusing member, and imaging optics for transmitting the light to a measuring window. In order to provide for an arrangement which is durable and accurate even when used for measuring hot specimens where the light source is positioned far from the measuring window, the fiber bundle arrangement includes a novel combination of a first fiber bundle and a second fiber bundle.

20 Claims, 1 Drawing Sheet

(51) Int. Cl.
*G02B 6/04* (2006.01)
*G01N 21/43* (2006.01)

(58) Field of Classification Search
CPC .. G02B 5/0273; G02B 5/0278; G02B 5/0294; G02B 6/0015; G02B 6/0016; G02B 6/0018; G02B 6/002; G02B 6/0025; G02B 6/0033; G02B 6/0035; G02B 6/0036; G02B 6/0043; G02B 6/0045; G02B 6/0051; G02B 6/0061; G02B 6/0075; G02B 6/04; G02B 6/06; G02B 6/065; G02B 6/08; G02B 6/25; G02B 6/0008; G01N 21/41; G01N 21/4133; G01N 21/43; G01N 21/431; G01N 2021/414; G01N 2021/4146; G01N 2021/4153; G01N 2021/416; G01N 2021/432; G01N 2021/433; G01N 2021/434; G01N 2021/435; G01N 2021/436; G01N 2021/437; G01N 2021/438

See application file for complete search history.

(56) References Cited

U.S. PATENT DOCUMENTS

| | | | | |
|---|---|---|---|---|
| 3,707,030 A | * | 12/1972 | Hunter | G01J 3/02 29/419.1 |
| 4,247,165 A | | 1/1981 | Versluis | |
| 4,904,049 A | * | 2/1990 | Hegg | C03B 37/15 385/116 |
| 4,973,128 A | | 11/1990 | Hodges | |
| 5,029,975 A | | 7/1991 | Pease | |
| 5,518,863 A | * | 5/1996 | Pawluczyk | G02B 3/005 216/24 |
| 5,680,492 A | * | 10/1997 | Hopler | G02B 6/262 385/119 |
| 5,754,719 A | * | 5/1998 | Chen | G02B 6/262 385/34 |
| 6,290,382 B1 | | 9/2001 | Bourn et al. | |
| 6,496,620 B1 | * | 12/2002 | Chen | G02B 6/02033 385/31 |
| 6,796,697 B1 | * | 9/2004 | Bragg | G01N 21/8806 362/268 |
| 8,967,845 B2 | * | 3/2015 | Bennett | G02B 6/001 362/556 |
| 9,632,025 B2 | | 4/2017 | Kamrat | |
| 2015/0055915 A1 | * | 2/2015 | Logunov | G02B 6/04 385/31 |
| 2019/0212491 A1 | * | 7/2019 | Greene | B60Q 1/0011 |

FOREIGN PATENT DOCUMENTS

| | | |
|---|---|---|
| JP | 3451526 B2 | 9/2003 |
| JP | 2011041758 A | 3/2011 |

OTHER PUBLICATIONS

Office Action dated Jan. 10, 2019, by the Finnish Patent Office for Application No. 20185566.

* cited by examiner

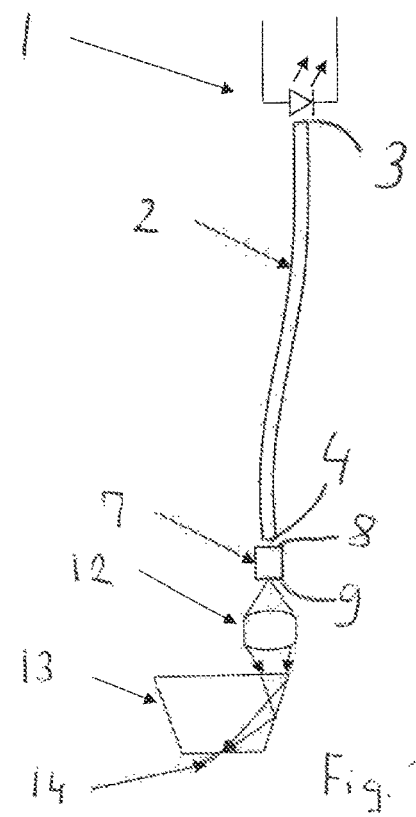
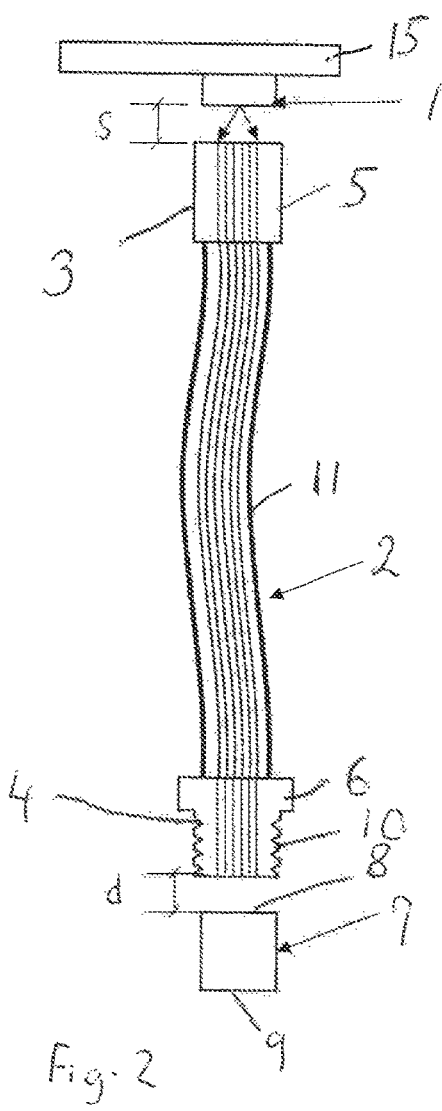
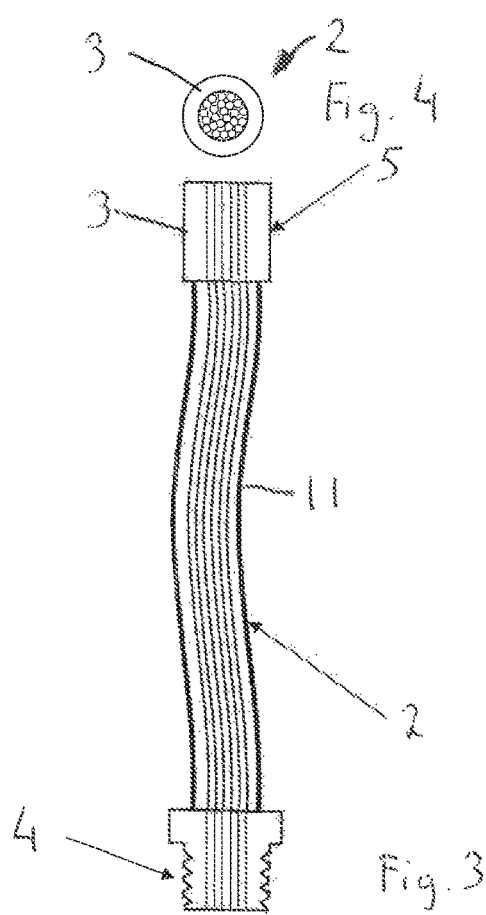
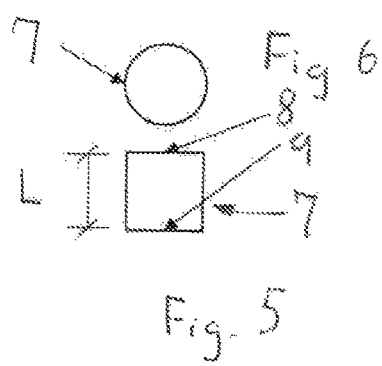

LIGHT ARRANGEMENT FOR AN OPTICAL DEVICE FOR MEASUREMENT OF AN INDEX OF REFRACTION, AND A REFRACTOMETER

BACKGROUND OF THE INVENTION

The invention relates to a light arrangement for an optical device for measurement of an index of refraction, comprising a light source, a fiber bundle arrangement for transmitting light from the light source, a diffusing member for receiving light from the light source and creating an even light distribution, and optics for receiving light from the diffusing member and for transmitting the light to a measuring window. The invention relates also to a refractometer having a light arrangement and an optical device for measurement of an index of refraction.

This type of light arrangement is known from U.S. Pat. No. 9,632,025 B2. A problem with known light arrangements is that they are prone to braking when they are used for measuring indexes of refraction from hot substances, where the temperature of the substances exceeds 100° C. More specifically, the light source may, owing to overheating, break if the light source is a light emitting diode. If the light source is arranged at a long distance from the prism and its measuring surface to prevent overheating of the light source, the fiber bundle becomes long and prone to breaking owing to impacts and vibration. Also, other electronical components then the light source may break in high temperatures. Another problem with a long fiber bundle arrangement is that its alignment with respect to the prism and its measuring surface is difficult to carry out.

BRIEF DISCLOSURE OF THE INVENTION

An object of the present invention is thus to provide a light arrangement for an optical device for measurement of an index of refraction, said light arrangement solving the abovementioned problems and which advantageously can be used for measurements of an index of refraction from hot substances. For this purpose the present invention puts forward a light arrangement for an optical device which is characterized in that the fiber bundle arrangement comprises a combination of a first fiber bundle and a second fiber bundle, the first fiber bundle comprising individual fibers arranged displaceable in relation to each other providing flexibility in the form of bendability for the first fibre bundle, the second fiber bundle comprising individual fibers attached to each other in such a way that individual fibers which are adjacent to each other at a first end of the second fiber bundle are adjacent to each other at a second end of the second fibre bundle, the second end of the second fibre bundle being opposite to the first end of the second fibre bundle, a first end surface of the fibers at the first end of the second fiber bundle being mat surfaced and a second end surface of the fibers at the second end of the second fiber bundle being mat surfaced for creating an even light distribution and forming said diffusing member, and the first fiber bundle being arranged closer to the light source than the second fiber bundle and being arranged to transfer light to the first end of the second fiber bundle.

The measuring window is preferably prismatic, preferably formed by a prism.

The first fiber bundle may preferably consist of low cost glass fibers without a need that the fibers are arranged. Preferably, the fibers of the first fiber bundle are non-arranged, this evening out irregularities of spatial distribution of the light from the light source of the providing an even angular distribution to the measuring surface.

Preferred embodiments of the invention are disclosed in the dependent claims.

The invention is based on the idea of providing a fiber bundle arrangement comprising a combination of a flexible, impact and vibration resistant first fiber bundle by which the light source can be positioned far away from the measuring window and exactly in relation to the measuring window in order to prevent the light source from being overheated from the heat generated by a hot process solution, or hot other specimen, to be measured, and a stiff and short second fiber bundle by which one can obtain an even light distribution for different angles of departure.

Major advantages of the light arrangement of the invention is that it has a good resistance against impacts and vibration even if the light source is positioned far away from the measuring window, and it enables accurate measurements without a need to position the light source in line with the axis of the lighting optics applied.

BRIEF DESCRIPTION OF THE DRAWING

In the following the invention will be described in greater detail by means of a preferred embodiment with reference to the accompanying drawing, in which FIG. 1 is shows a general view of the light arrangement employed for a refractometer, FIG. 2 shows in more detail the upper part of the components of the light arrangement of FIG. 1, FIG. 3 shows the first fiber bundle of the light arrangement of FIG. 1 seen in a side view, FIG. 4 illustrates the upper end of the first fiber bundle seen from above, in the length direction of the first fiber bundle, and FIGS. 5 and 6 show the second fiber bundle of the light arrangement of FIG. 1 seen in a side view and from above, respectively.

DETAILED DESCRIPTION OF THE INVENTION

FIG. 1 shows a light arrangement for an optical device for measurement of an index of refraction. The shown components represent main parts of a refractometer for measuring e.g. process liquids. For sake of simplicity no components for analysing light have been drawn in the Figure. In FIG. 1, reference numeral 1 indicates a light source in the form of a light emitting diode. The light emitting diode can preferably be of the type generating the wavelength of approximately 589 nm. The light source 1 can alternatively be a light source providing said wavelength by e.g. filtering it (by an interference filter) out from daylight.

A first fiber bundle is designated with reference numeral 2. The first fiber bundle 2 comprises a plurality of individual fibers, preferably multimode optical fibers, arranged displaceable in relation to each other providing bendability to the fiber bundle. This means that the fiber bundle 2 can flex in such a way that one can change the position of the second end 4 of the fiber bundle 2 in relation to the first end 3 of the fiber bundle. The fibers of the fiber bundle 2 do not break when bending the fiber bundle, neither does the fiber bundle break owing to impacts or vibration. The diameter of the individual fibers is typically 125 µm, which covers usual applications for the light arrangement of the invention. More generally, fibers having a diameter of 100 to 150 µm are preferable for being used. The fibers can preferably be e.g.

conventional glass optical fibers. The number of fibers in the bundle can e.g. be 100, and preferably 50 to 200. The fibers in the first end 3 of the fiber bundle 2 are attached to each other, preferably by gluing or by casting in resin. The same applies to the fibers at the second end 4 of the fiber bundle 2. Preferably, the ends 3, 4 of the fiber bundle 2 are provided with sleeves 5, 6, especially if the fibers are glued, see FIG. 2 which shows the fiber bundle 2 enlarged and in more detail. The sleeves 5, 6 protect the ends 3, 4 and allow for fixing the ends of the fiber bundle 2 in desired position. The sleeves can be made from metal, preferably brass, or alternatively e.g. from plastics. Preferably, the fibers in the fiber bundle 2 are non-arranged, i.e. adjacent fibers at the first end 3 of the fiber bundle 2 are typically not adjacent at the second end 4 of the fiber bundle. This evens out irregularities of spatial distribution from the light source 1. The length of the fiber bundle 2 can vary depending on application. If necessary, it can be very long, e.g. one meter.

Reference numeral 7 designates a diffusing member in the form of a second fiber bundle. The second fiber bundle 7 comprises a plurality of individual fibers. The number of fibers is typically dozens of hundreds. The diameter of the individual fibers is smaller than the diameter of the fibers of the first fiber bundle 2. The fibers of the second fiber bundle 7 have a diameter of typically 8-12 μm. However, it is likely that diameter values deviating from said range can be used. The individual fibers are interconnected between a first end 8 of the fiber bundle and a second end 9 of the fiber bundle, along the length of the fiber bundle, providing—in contrast to the first fiber bundle 2—a stiff fiber bundle. The individual fibers adjacent to each other at the first end 8 of the second fiber bundle 7 are adjacent to each other at the second end 9 of the second fiber bundle, i.e. the fibers of the fiber bundle are arranged. This means that the second fiber bundle 7 is capable of producing an image and can, consequently, be called an imaging bundle. The end surface formed by the fibers at the first end 8 of the second fiber bundle 7 does not necessarily be aligned with (parallel with) the end surface formed by the fibers at the second end 9 of the second fiber bundle 7. The length of the second fiber bundle 7 is shorter than the length of the first fiber bundle 2. Typically, the length is only fraction of the length of the first fiber bundle 2. Thanks to this, the second fiber bundle 7 is not prone to breaking as a consequence of impacts and vibration, and furthermore, the costs for manufacturing the second fiber bundle 7 are low. The length L (see FIG. 5) of the second fiber bundle 7 is preferably 3 to 15 mm and the diameter thereof is preferably 1 to 5 mm, and even more preferably 2 to 4 mm. If the length of the fiber bundle 7 substantially exceeds 15 mm, the durability of the fiber bundle against impacts and vibration becomes poor. The second fiber bundle 7 must (in use) be positioned and fixed in relation to the prism 13. Support structures for such fixation are, however, not shown in the drawings, because they can be of conventional type.

In FIG. 2 reference numeral 15 designates a circuit board. As can be seen from the figure, there is a gap S between the light source 1 and the first end 3 of the first fiber bundle 2. The gap S is in practice an air gap of 0.2 to 1 mm, preferably about 0.5 mm. As clearly seen from FIG. 2, there is also a gap d, in practice an air gap, between the second end 4 of the first fiber bundle 2 and the first end 8 of the second fiber bundle 7. The gap d is preferably 0.3 to 5 mm. If the gap d is bigger than 4 to 5 mm, light energy cannot be effectively transferred from the first fiber bundle 2 to the second fiber bundle 7, because the light does not effectively hit the second fiber bundle. The bigger the gap d, the more light goes lost.

From FIG. 2 one can see that the sleeve 6 is provided with threads 10, preferably external threads. These threads 10 are for attaching the end 4 of the fiber bundle 2 to a support member (not shown) for positioning the end 4 of the fiber bundle 2 fixedly in relation to the second fiber bundle 7. Applying a threaded sleeve 6 improves, in practice, the results of the measurements carried out with the measuring device.

The first fiber bundle 2 is surrounded by a flexible protective tube 11 having good bendability. Preferably, the tube 11 has a length which at least essentially corresponds to the length of the individual fibers. The tube 11 provides for mechanical protection of the fibers of the fiber bundle 2, it protects the fibers e.g. against impacts. The tube 11 also prevents light from escaping laterally out from the fiber bundle—especially if the fiber bundle 2 is heavily bent (curved) in use. The tube 11 can preferably be made from silicone, which is very flexible and can also be used in relatively high temperatures (up to 200° C.), if necessary.

FIG. 4 shows as an end view from above the first end 3 of the first fiber bundle 2. The end surfaces of the fibers, seen in the figure, are planar and glossy to provide for efficient transfer of light. The same applies to the end surfaces of the fibers at the second end 4 of the fiber bundle 2. The scratch and dig number for the end surfaces of the fibers is 60/40 rated according to the U.S. Military Performance Specification MIL-PRF-13830B.

FIG. 6 shows an end view of the second fiber bundle 7. The end surfaces of the fibers at the first end 8 of the fiber bundle 7 is mat surfaced. The same applies to the fibers at the second end 9 of the fiber bundle 7. The mat surface is achieved by grinding the ends of the fibers. The grinded surfaces provide for a random variation which mixes the angular distribution of the light. Owing to the mat surfaces, the second fiber bundle 7 forms a diffusing member which functions as a diffuse light source which provides for an even light distribution at different measuring angles.

Going back to FIG. 1, reference numeral 12 designates imaging optics 12 for receiving light from the fiber bundle 7 (from the diffusing member) and for transferring the light to a measuring surface 14 formed by a prism 13. At the measuring surface 14 a total internal reflection takes place. The prism 13 can be called a measuring prism. One may say that the first flexible fiber bundle 2 is used for bringing the light from the light source 1 closer (although not physically closer) to the measuring prism 13. As the imaging optics 12 and prism 13 are components readily known for persons skilled in the art, these components are not explained in more detail in this connection. The light source 1 can be positioned in such a way that it is not in line with the other components of the imaging optics, as is readily seen in FIG. 1. This makes it easy to install the light arrangement for different measurement environments. Although the light arrangement shown in FIG. 1 preferably is applied in a refractometer, FIG. 1 does not show components (such as e.g. lenses and a camera) needed for analysing light. An essential feature of the invention, when applied to a refractometer, is, however, that it can provide for an even light distribution at the measuring surface 14 of the prim 13, and more generally to a measuring window. This is important because total reflection occurs at a specific angle and it is desired that there is light on the measuring surface around said specific angle. Accuracy is, naturally, strived at and required for the optical measuring device.

The present invention has above been disclosed by only one embodiment. Therefore, it is emphasized that the present invention can be implemented in detail in many various ways within the scope of protection defined by the attached claims. Accordingly, e.g. the fibers of the first fiber bundle need not be multi mode fibers, the fibers need not be non-arranged, and need not be made of glass.

The invention claimed is:

1. Light arrangement for an optical device for measurement of an index of refraction, the light arrangement comprising:
   a light source;
   a fiber bundle arrangement for transmitting light from the light source, the fiber bundle arrangement including a diffusing member for receiving light from the light source and creating an even light distribution; and
   imaging optics for receiving light from the diffusing member and for transmitting the light to a measuring window of the optical device, wherein the fiber bundle arrangement has a combination of a first fiber bundle and a second fiber bundle, the first fiber bundle including individual fibers arranged displaceable in relation to each other providing flexibility for bendability of the first fibre bundle, the second fiber bundle including individual fibers attached to each other in such a way that individual fibers which are adjacent to each other at a first end of the second fiber bundle are adjacent to each other at a second end of the second fibre bundle, the second end of the second fibre bundle being opposite to the first end of the second fibre bundle, a first end surface of the fibers at the first end of the second fiber bundle being mat surfaced and a second end surface of the fibers at the second end of the second fiber bundle being mat surfaced providing for a random variation that mixes an angular distribution of light for creating an even light distribution and forming said diffusing member, and the first fiber bundle being arranged closer to the light source than the second fiber bundle and being arranged to transfer light to the first end of the second fiber bundle.

2. A light arrangement according to claim 1, wherein the measuring window is prismatic.

3. A light arrangement according to claim 1, comprising:
   a gap between a second end of the first fiber bundle and the first end of the second fiber bundle, said gap being 0.3 to 5 mm.

4. A light arrangement according to claim 1, wherein an end surface of the fibers at a first end of the first fiber bundle and an end surface of the fibers at a second end of the first fiber bundle are planar and glossy for providing efficient transfer of light from the first end of the first fiber bundle to the second end of the first fiber bundle and to the first end of the second fiber bundle.

5. A light arrangement according to claim 4, wherein a scratch and dig number for end surfaces of the fibers of the first fiber bundle is 60/40 rated according to U.S. Military Performance Specification MIL-PRF-13830B.

6. A light arrangement as claimed in claim 1, wherein fibers in the first fiber bundle are non-arranged.

7. A light arrangement as claimed in claim 1, wherein individual fibers of the first fiber bundle are multi mode fibers.

8. A light arrangement as claimed in claim 1, wherein individual fibers of the first fiber bundle have a diameter of 100-150 μm.

9. A light arrangement as claimed in claim 1, wherein the first fiber bundle is surrounded by a flexible protective tube.

10. A light arrangement as claimed in claim 1, wherein a first end and a second end of the first fiber bundle are each provided with an end sleeve where the fibers have been interconnected.

11. A light arrangement as claimed in claim 10, wherein the end sleeve of the second end of the first fiber bundle is provided with threads for attaching to a support member for positioning the second end of the first fiber bundle fixedly in relation to the second fibre bundle and a prism.

12. A light arrangement as claimed in claim 1, wherein a number of fibers in the first fiber bundle is 50 to 200.

13. A light arrangement as claimed in claim 1, wherein the individual fibers of the second fiber bundle have a diameter of 8 to 12 μm.

14. A light arrangement as claimed in claim 1, wherein a length of the second fiber bundle is shorter than a length of the first fiber bundle.

15. A light arrangement as claimed in claim 14, wherein the length of the second fiber bundle is 3 to 15 mm.

16. A light arrangement as claimed in claim 14, wherein a diameter of the second fiber bundle is 1 to 5 mm.

17. A light arrangement as claimed in claim 1, wherein the imaging optics comprises:
   at least one lens for imaging a surface of the second end of the second fiber bundle to the measuring window.

18. A light arrangement as claimed in claim 1, wherein the light source is configured to generate a light wavelength of substantially 589 nm.

19. A light arrangement as claimed in claim 18, wherein the light source comprises:
   a light emitting diode.

20. A refractometer comprising:
   an optical device for measurement of a index of refraction with a light arrangement as recited in claim 1, the measuring window having a surface where a total internal reflection takes place.

* * * * *